United States Patent
Blower, Jr. et al.

(10) Patent No.: US 6,323,852 B1
(45) Date of Patent: *Nov. 27, 2001

(54) METHOD OF ANALYZING ORGANIZING AND VISUALIZING CHEMICAL DATA WITH FEATURE HIERARCHY

(75) Inventors: Paul E. Blower, Jr., Columbus; Wayne P. Johnson, Upper Arlington; Glenn J. Myatt, Columbus, all of OH (US)

(73) Assignee: Leadscope, Inc., Columbus, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/224,976

(22) Filed: Jan. 4, 1999

(51) Int. Cl.$^7$ ............... G06F 15/00; G06F 3/00
(52) U.S. Cl. .................... 345/326; 345/968
(58) Field of Search ........................ 345/326, 335, 345/339, 340, 346, 356, 968; 707/1, 2, 3; 700/91, 266; 709/203

(56) References Cited

U.S. PATENT DOCUMENTS

| | | | |
|---|---|---|---|
| 4,811,217 | 3/1989 | Tokizane et al. | 707/3 |
| 5,249,137 * | 9/1993 | Wilson et al. | 703/2 |
| 5,321,804 * | 6/1994 | Kusaba et al. | 707/509 |
| 5,386,507 * | 1/1995 | Teig et al. | 345/348 |
| 5,418,944 | 5/1995 | DiPace et al. | 707/3 |
| 5,555,366 * | 9/1996 | Teig et al. | 711/169 |
| 5,577,239 | 11/1996 | Moore et al. | 707/3 |
| 5,950,192 * | 9/1999 | Moore et al. | 707/3 |
| 6,125,383 * | 9/2000 | Glynias et al. | 709/202 |

* cited by examiner

Primary Examiner—Crescelle N. dela Torre
(74) Attorney, Agent, or Firm—Standley & Gilcrest LLP

(57) ABSTRACT

The present invention is directed to a method and system for displaying correlations between structural Features of a molecule and the biological or physical properties of the molecule. A unique feature of the present invention is that the user has a convenient way to select and explore a succession of interesting subsets and to interactively control the contents of each subset using filters. The medicinal chemist can thereby use his or her intuition and experience to guide the process of drug selection. In a preferred embodiment, the method and system of the invention uses at least four coordinating panels which comprise: 1) one or more first panels containing a series of molecular structural Feature or ranges of properties, such as molecular weight; 2) a second panel showing a graph (e. g., a bar graph) of the contents of the set shown in the first panel, the size of the bar graph may represent the number of members of the set containing the Feature or the biological or physical property of the set; 3) a third panel containing at least one interactive control, i.e. a two-ended slider, wherein each control corresponds to a biological or physical property of the set; and 4) a fourth panel for selecting and adjusting the graphical display of the biological or physical property displayed in the second panel.

11 Claims, 12 Drawing Sheets

METHOD OF ANALYZING ORGANIZING AND VISUALIZING CHEMICAL DATA WITH FEATURE HIERARCHY

TECHNICAL FIELD

The present invention is directed to software that allows medicinal chemists to analyze, organize and visualize large sets of chemical compounds and associated biological and physical property data, that have potential as therapeutic agents.

BACKGROUND OF THE INVENTION

Medicinal chemists are faced with the continuing process of enhancing the desirable attributes of a wide range of pharmaceuticals and potential drug candidates. Typically, this process comprises the steps of:

(a) acquiring compounds for testing;

(b) performing one or more biological assays and, possibly, analysis of physical properties;

(c) examining the results and formulating a structural hypothesis that explains compound activity; and (d) designing a focused compound library to test the structural hypothesis.

At any one time, a chemist may receive assay data on a set of up to 10,000 compounds in step (c). His or her task is to determine what molecular feature or combination of features are responsible for the compounds biological or physical activity in order to formulate a structural hypothesis for such activity and thereby design a focused library for testing of the hypothesis. There are a number of software products presently on the market that provide some help to the medicinal chemist, including packages from Daylight Chemical Information Systems, Inc. of Mission Viejo Calif.; MDL Information Systems, Inc. of San Leandro Calif.; Oxford Molecular Group of Oxford, England; Molecular Simulations, Inc. of San Diego Calif.; Synopsis Scientific Systems, Ltd. of Leeds, England; and Tripos, Inc. of St. Louis Mo.

A popular type of software tool available today is classified as "molecular spreadsheets," modeled on spreadsheets for financial applications. The spreadsheet typically has one row for each substance or compound and one column which will have a structural diagram for the substance. Other columns of this spreadsheet will have substance identifiers and/or other bookkeeping information, biological response data and experimental or calculated property data such as molecular weight. The medicinal chemist will have to access several different corporate and/or project files to load desired information into the spreadsheet.

With chemical structures, biological activity and other data loaded into a molecular spreadsheet, the medicinal chemist will then sort on activity, bringing the most active compounds to the top and begin visually examining those compounds with the highest activity, one at a time. After the chemist has inspected 50–100 compounds, he or she will probably have noticed some substructure that seems to occur frequently and hypothesize that that substructure is partially responsible for the compound's activity. The chemist could verify this by the following procedure:

(1) formulate a substructure search query corresponding to the hypothesized active structure and conduct the substructure search;

(2) determine the numbers of active and inactive compounds that contain the structural feature; and (3) perform a statistical calculation on the mean activity of compounds containing the structure versus mean activity of the full set.

Each step in this process will require a different software program and a significant amount of the chemist's time. The process could then be repeated over and over until the medicinal chemist concludes that the evidence supports his or her hypothesis.

Presently available molecular spreadsheets force the chemist to deal with compounds one at a time and are, thus, limited to small sets. Furthermore, because the iterative process of verifying a structural hypothesis outlined above is so cumbersome and time-consuming, the chemist is forced to cut corners. Often this means that the inactive compounds are simply discarded. Eliminating inactive compounds precludes the opportunity to learn from negative results.

The structure of a chemical substance is responsible for its biological activity and physical properties. There is a large body of literature [8] and a number of commercially available software packages for correlating structural descriptors or quantitative structure-activity relationships (QSAR Programs). Two of the newest and most popular commercial programs are Comparative Molecular Field Analysis (CoMFA) and HQSAR, both from Tripos Assoc., St. Louis Mo.

There are usually three steps to QSAR analysis: 1) selection of a set of molecular descriptors, 2) calculation of the molecular descriptors for each substance; and 3) statistical analysis of descriptor/activity data. A wide variety of structural descriptors have been used, including generalized atom-pairs, atom-pair fingerprints, substructure search screens, two dimensional and three dimensional shape descriptors, partial atomic charges, and topological indices. In the HQSAR program, molecular structures are dissected into all possible connected atom-bond fragments of predetermined size (number of atoms). Once molecular descriptors have been identified, a statistical method is used to generate a QSAR model relating descriptors to activity. Commonly used statistical methods are multiple linear regression, principal component analysis and partial least squares.

CoMFA uses variance in field strengths around a set of aligned three dimensional structures to describe the observed variance in biological activity. Although CoMFA is the most popular and highly regarded three dimensional QSAR method, it requires expert knowledge. The chemist must make decisions regarding conformation and relative alignment which can be difficult and complex, especially with structurally diverse molecules.

Another approach to structure-activity relations (SAR) is known as "recursive partitioning." Computer algorithms have been developed [9] that partition a set of chemical structures into subsets based on a statistical calculation comparing subsets which contain 0, 1, or more instances of a predefined structural feature. Then the procedure is recursively reapplied to the newly created subsets until some statistical threshold is exceeded. The procedure produces a dendrogram where the nodes are compound sets. A dendrogram is a branching diagram representing a hierarchy of categories based on degree of similarity or number of shared characteristics. The root node is the full compound set or parent set, and the offspring of any node is a partitioning of the parent set. The structural features that have been used are similar to those used for clustering and conventional SAR. There is no provision for the chemist to participate in this partitioning process in the prior art programs.

There are a number of problems with integrating commercially available structure-activity software into the iterative drug discovery process of design, synthesis, testing, analysis and hypothesis formulation. For example, the molecular descriptors used for correlations in the available software are difficult for medicinal chemists to use for designing a compound set for the next iteration of the discovery process. Further, many of the commercial software packages require an expertise outside the typical medicinal chemist's knowledge and experience. The raw assay results will typically need to be first processed by a computational chemist. This is time-consuming and the medicinal chemist will not be able to participate and use his or her intuition and experience to guide the process. Another problem with presently available software packages is that there are a tremendous number of molecular descriptors to choose from, and selection of an optimal descriptor set can be time-consuming and may require assistance of a statistician to avoid problems such as colinearity and over-selection of descriptors.

BACKGROUND ART

U.S. Pat. No. 5,577,239 to Moore et al. discloses a chemical structure search system utilizing relational database technology. The Moore et al. method generates computer search keys for every atom in a chemical structure for searching chemical structures stored in a relational database. In a first step the user chooses a starting atom in an input chemical structure and then adds a code for the starting atom to a key string. Bonds that are adjacent to the starting atom are then ordered and codes for the ordered bonds are added to the key string. The search key is generated based upon the codes for the ordered bonds and the atoms. This reference fails to suggest or disclose a method for the systematic, exhaustive substructural analysis of datasets of chemical substances by predefined structural features. This reference also fails to suggest a method or system that provides for: 1) the browsing of contents of the dataset; 2) statistically correlating the structural features with one or more biological properties; and 3) comparing the contents of two or more datasets of chemical substances.

U.S. Pat. No. 4,811,217 to Tokizane et al. discloses a method of storing and searching chemical structure data using a query chemical structure by examining the match or analogy between the query and the stored structure data. The Tokizane et al. method comprises the steps of: 1) assigning numbers to each chemical unit to be stored, storing the numbers in a connection table, storing attribute data (describes the chemical characteristics of the chemical unit) in an attribute table; 2) assigning numbers to the query chemical structure and storing them in a connection table and an attribute table; and 3) examining the match or analogy of the query structure attribute table with the attributes of the stored chemical structure table using a mathematical condition defined in advance. This reference fails to disclose or suggest a system or method wherein correlation between molecular substructural features and biological or physical properties can be displayed and wherein the user can dynamically adjust the members of the underlying molecular set.

U.S. Pat. No. 5,418,944 to DiPace et al. discloses a knowledge-based molecular retrieval system and method using a hierarchy of molecular structures in the knowledge base. The DiPace et al. method comprises the steps of: 1) defining a hierarchy of molecular residues, functional groups and atomic structures (structural levels); 2) building a dictionary of molecular fragments for each structural level; 3) collecting chemical and physical properties for each molecular fragment and building a knowledge base; 4) selecting a structural level of molecular representations based on similarity to an input reference; 5) performing a matching between the input reference and the molecular representations at the level selected in step 4; and 6) selecting all the molecular structures similar to the input reference and outputting all of the selected molecular structures. The DiPace et al. reference also discloses a molecular structure retrieval system which comprises: 1) a first storage means for storing a hierarchical description of molecular structures as molecular fragments in different structural levels; 2) a second storage means for storing known molecular fragments and physical and chemical properties associated with the fragments; 3) a recognizing means for recognizing the fragments in an input reference so as to represent them in a hierarchical description; 4) an analyzing means for selecting a structural level of molecular structures based on similarity to the input reference; and 5) a matching means that performs a matching of the fragments of the input reference against the fragments stored in the first storage means. This reference fails to disclose a method for representing subsets of an underlying substance set corresponding to substructural features and physical/biological properties. The present invention in contrast to the DiPace et al. method and systems, allows the user to rapidly determine the members of the underlying substance set that contain a given structural feature and fall within specified property values and/or biological activities. Further, the DiPace et al. patent does not disclose a system that provides for rapidly recalculating the statistical deviation of the physical property and/or the biological activity from an expected value.

One major aspect of the present invention is intended to remedy problems with existing commercial software for analyzing large quantities of structure-activity data. With this and other aspects, the advantages and features of the invention will become apparent and more clearly understood by reference to the detailed description of the invention, the appended claims and the drawings attached hereto.

SUMMARY OF THE INVENTION

The computer system of the present invention generally comprises 1) a template library which lists definitions for the structural classes and subsequent subclasses (called features) of certain chemical compounds; 2) a compilation process which is used to create compiled projects by analyzing chemical structures, and biological and physical property data; and 3) an exploration tool which comprises a user interface (UI). The UI allows users to both see and manipulate the underlying information on structural features and associated properties in order to focus on what is relevant and to dynamically reorganize the project.

An important aspect of this invention is that the user has no means for entering a structural query into the system. The compilation aspect of this system sets it apart from the prior art.

Thus, there is disclosed, a computer system for visualizing and exploring the contents of a dataset of chemical structures and related properties using structural features, comprising:

(a) a client computer program that functions as a user interface;
(b) a (possibly separate) server computer program that functions as a database server and computational engine; and
(c) a compiled database of chemical structures and related properties.

The system and method employ a user interface (UI) which incorporates computer visualization techniques that have been previously developed [1–4].

In a preferred embodiment of the invention, the UI comprises at least three coordinating panels or windows on the computer screen:
(a) at least one panel (the first panel) containing a series of structural features (possibly arranged in a class hierarchy) or ranges of certain substance properties;
(b) a second panel showing a representation, such as a graph, of the contents of the underlying substance set relative to the structural features or properties in the first panel; and
(c) a third panel containing at least one interactive control that allows the user to dynamically adjust the members of the underlying substance set.

In a more preferred embodiment of the invention, the UI contains a fourth panel for selecting and adjusting the meaning and appearance of the graphical elements displayed in the second panel.

There is further disclosed a method (M1) for selecting and exploring subsets of a project or subproject, said method comprising the steps of: (a) activating a client computer program which functions as a UI as hereinafter further described (b) loading a compiled project of substances and associated properties, (c) and manipulating the interactive controls of the UI, as hereinafter described, in any combination or sequence, to result in at least one of the following: to expose subclasses of structural features, to select subsets of the underlying substance set or a previously selected subset, to expose greater detail of the substances in a selected subset, and to restrict the properties of a substance set or a selected subset. As used here and in the claims, the term project means the initial project and any subprojects derived therefrom.

There is further disclosed a method for statistically correlating sets of chemical compounds containing certain structural features with one or more properties of the substances, said method comprising the steps of method M1 wherein step (b) additionally comprises the steps of: (i) selecting at least one substance property for correlation, and (ii) selecting a statistical measure.

There is further disclosed a method for comparing the similarity and differences of two or more datasets of chemical substances, said method comprising the steps of method M1 wherein step (b) additionally comprises the step of loading at least one additional compiled project of substances and associated properties.

There is further disclosed a method (M2) for determining the members of a substance set that satisfy given structural feature and property constraints, said method comprising the steps of: (a) associating with each property value range (or category) a bit vector that designates the substances that fall in said property category; (b) constructing a property filter vector corresponding to the property control settings; (c) constructing a composite property bit vector that designates the set of substances which satisfy all property restrictions; (d) associating with each structural feature a bit vector that designates the substances containing said feature; and (e) constructing the bit vector that designates the substances containing said structural feature and satisfying all property restrictions.

There is further disclosed a method for correlating substance activity with structural features for substances satisfying given property constraints, said method comprising the steps of: (a) applying the steps of methods M2 resulting in a composite property bit vector and several structural feature bit vectors; (b) associating with each activity category a bit vector that designates the substances that fall in said activity category; (c) constructing a set of activity-property bit vectors which partition the set of substances which satisfy all property restrictions among the several activity categories; (d) calculating the expected activity of any subset from the one-bits in each of the activity-property bit vectors; (e) for each structural feature, constructing a set of activity-property-feature bit vectors which designates the number of substances that contain said feature, are in said activity category, and satisfy all property restrictions; (f) calculating the mean activity of said feature subset from the one-bits in said set of activity-property-feature bit vectors; and (g) calculating a statistical measure comparing the mean activity of said feature subset with said expected activity value.

DETAILED DESCRIPTION OF THE INVENTION AND PREFERRED EMBODIMENTS

The present invention also discloses a set of software tools comprising:
(1) an exploration tool or user interface designed to utilize compiled structural features and associated properties to provide a fast, interactive and dynamic way of performing information analysis tasks;
(2) an analysis process which enables a user to create projects by analyzing chemical structures, and biological and physical property data for access during run-time exploration; and
(3) a template library listing the structural classes and subsequent subclass features of certain chemical compounds.

User Interface

Figure 1:
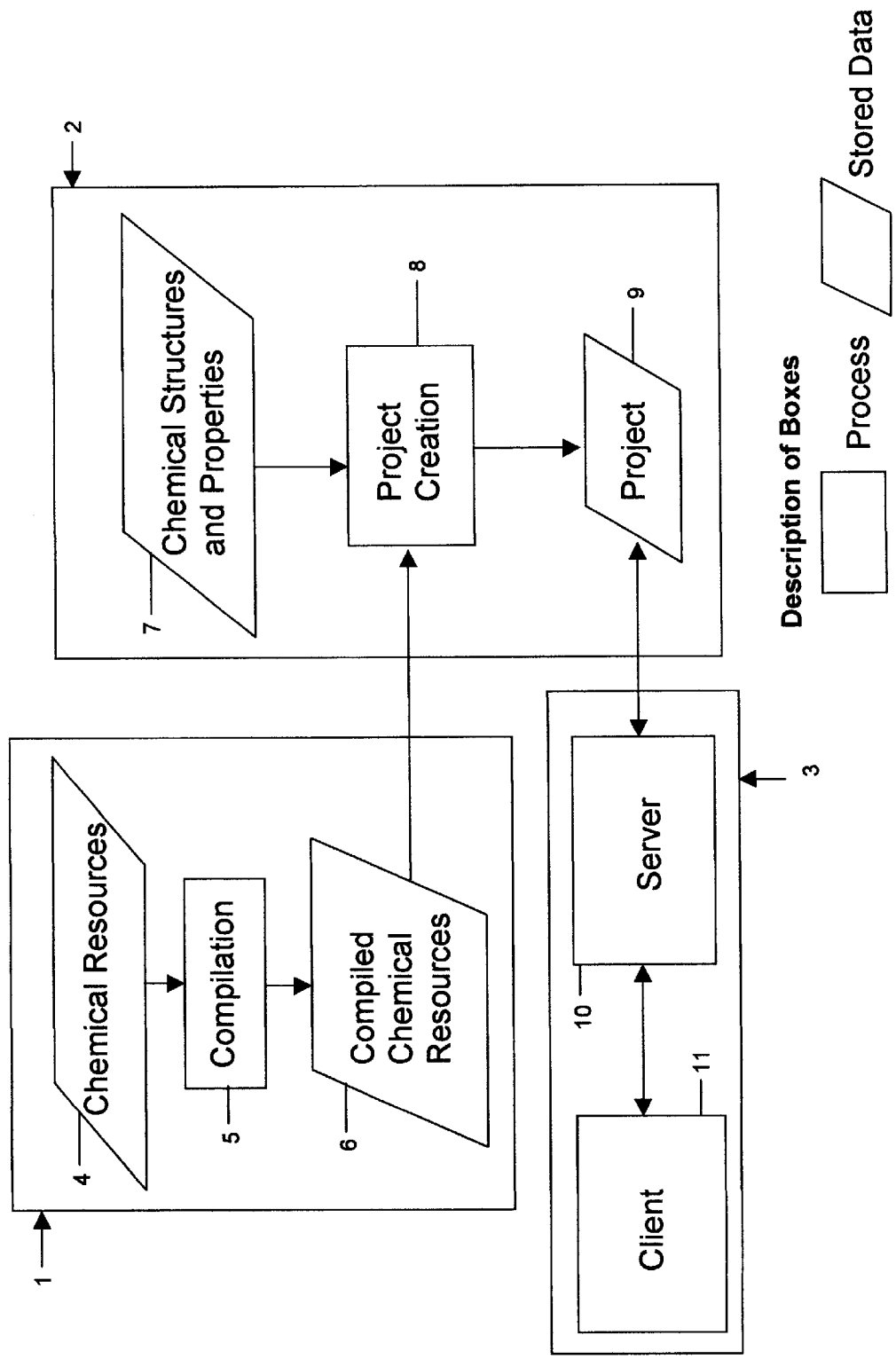
FIG. 1 is a diagram of the major subsystems in the present invention.
Figure 2:
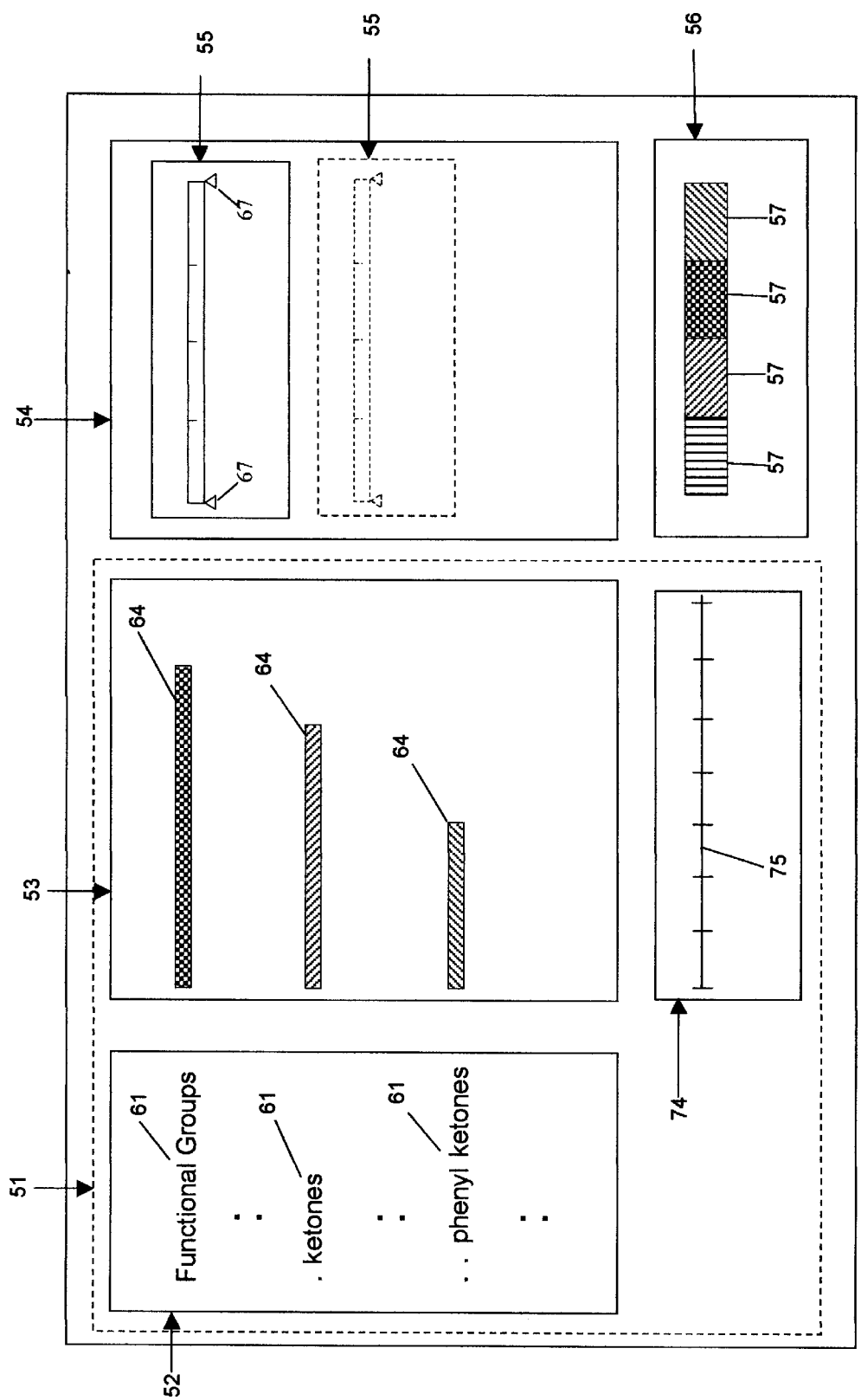
FIG. 2 is a schematic diagram of the four panels of the UI.

With reference to FIG. 1, the exploration tool 3 uses a compiled database of structural features to provide a fast, interactive, and dynamic way of performing information analysis tasks. The exploration tool 3 has two major subsystems: 1) a server subsystem 10 which implements the analysis processing and handles requests for information from the client, and is further described in the next section; and 2) a client subsystem 11 which implements the user interface and supports the visualization of information and the tool's interaction with the user. In an embodiment of the invention as shown in FIG. 2, the IU comprises four coordinating panels or windows on the computer screen:
1. A first panel 52 containing a series of structural features or ranges of properties, such as molecular weight. The first panel may consist of one or more panels wherein the panels may be used to represent the axes of a graph depicting the contents of the substance set relative to the features 61 or properties. The panels may be arranged horizontally and/or vertically.

2. A second panel 53 showing a representation, such as a graph 64, of the contents of the underlying substance set (or sets in side-by-side comparisons) relative to the list(s) of structural features 61 or properties in said first panel 52. Each feature 61 in the visible list is represented by a graphical element 64, such as a bar, and each feature 61 and bar 64 are physically aligned and coordinated.

3. A third panel 54 containing a series of one or more interactive controls 55, such as a two-ended slider 67, where each control corresponds to a biological or physical property, such as molecular weight, or other categorical data, which may be calculated or experimental, of the underlying structure set. The slider may be marked with values of the property at regular intervals (such as 200, 400, 600 molecular weight units), and the user can adjust the control 55 to select a desired range of property values such as by moving one of the sliders 67. Use of a control 55 constrains the underlying substance set to the subset of substances with property values in the range displayed on the control 55, and the graphical display 64 in the second panel 53 is automatically modified to reflect this new subset. When the second panel 53 is a multi-dimensional feature/feature plot, then additional controls 55 may be added.

4. A fourth panel 56 (legend panel) is used for selecting and adjusting the meaning and appearance of the graphical elements 64 displayed in the second panel 53. For example, the user may select a biological or physical property, ranges or categories of property values, and associate a color or hatching pattern of each segment 57. In a similar fashion, the user may select statistical probability or standard deviation ranges and the color or pattern of each range 57.

The architecture of the UI consists of a set of components that provide the look-and-feel (called views) and a set of components that provide the data for one or more view components (called models). Beginning with the outermost view component, or window, a view may contain additional smaller views in order to break up the display area into increasingly smaller regions of control. While a view component manages what the user sees and the way it responds to user input in some area of the display, the data presented by a view comes from one or more model components.

The UI design adopts a notebook metaphor. Within an outer shell (window), an internal frame (notebook) is generated when a project is opened. The project's data is presented as tabbed pages of the notebook (sheets) as illustrated in FIG. 2 for the histogram sheet 51. Note that both the first panel 52 and the second panel 53 are logical components of the histogram notebook sheet 51. The major components of the histogram sheet and the scatterplot sheet are given in Tables 1 and 2. In addition to the tabbed sheets, the notebook contains two fixed areas, one for filters 54 and the other for legends 56.

TABLE 1

Components of the Histogram Sheet

Y-Axis
Histogram
NumberScale

TABLE 2

Components of the Scatterplot Sheet

Y-Axis
Scatterplot
X-Axis

FIG. 2 shows the structural features 61 of a substance set arranged in a hierarchy in the first panel 52, with each feature 61 displayed as a name or a chemical diagram. The graphical elements, such as histogram bars 64, in the second panel 53 may be used to represent a biological or physical property of the underlying subset. The length of a histogram bar 64, as measured by the number scale 74, may be used to represent the number of members of the underlying set containing the corresponding structural feature or property. The histogram bar 64 for a given structural feature 61 could be segmented such that the length of a segment indicates the number of substances containing the given feature in each property value range. In an analogous way, histogram bar segments can be used to depict categories or ranges of a biological response variable, such as $IC_{50}$ value. Alternatively, the user may choose a statistical measure such as probability or standard deviation ranges and set the color or pattern of each range using the legend panel 56.

In the preferred embodiment of the invention, the algorithm at the heart of the UI consists of the familiar loop: action—filter—encode—render. There are four steps in the computational loop.

Step 1. Action. A change in the display is triggered by some user action. Examples of actions include the selection of a new axis or filter, scrolling through the feature hierarchy, or the use of a slider 67 in a filter 55.

Step 2. Filter. Filter computation will be described separately below. The computation results in a subset that is then passed to the next step, along with other data, to be visually encoded.

Step 3. Encode. The output from the filtering step is passed to the legend component which may perform additional calculations using the information from the structures within or about the subset itself. For example, the standard deviation legend performs statistical analysis using the output subset and activity data imported into the project to calculate the standard deviation of this subset's activity as compared to a subset of equal size selected at random from the project's structure set. The result of this computation is encoded according to user settings in the legend panel 56 and passed to the function that renders and displays the data to the user.

Step 4. Render. Within the sheets for which filters apply, a rendering function uses data collected in a summary data structure to present the information to the user. For example, in the histogram view (FIG. 2), the number of structures in the output subset calculated during the filter step is used to determine the length of the bar 64. The color or hatching pattern 57 chosen by the legend 56 is used to shade the bar. Rendering of scatterplot cells is analogous.

In an embodiment of the invention, there are several novel techniques used to provide continuous feedback. Included in these techniques is a significant reduction in the computational processing required during exploration made possible by the use of projects of compiled structure and property data. The preferred embodiment of the invention makes extensive use of bit vectors as a representation for sets of objects (e.g., features, structures), property values, and categorical data.

Figure 3:
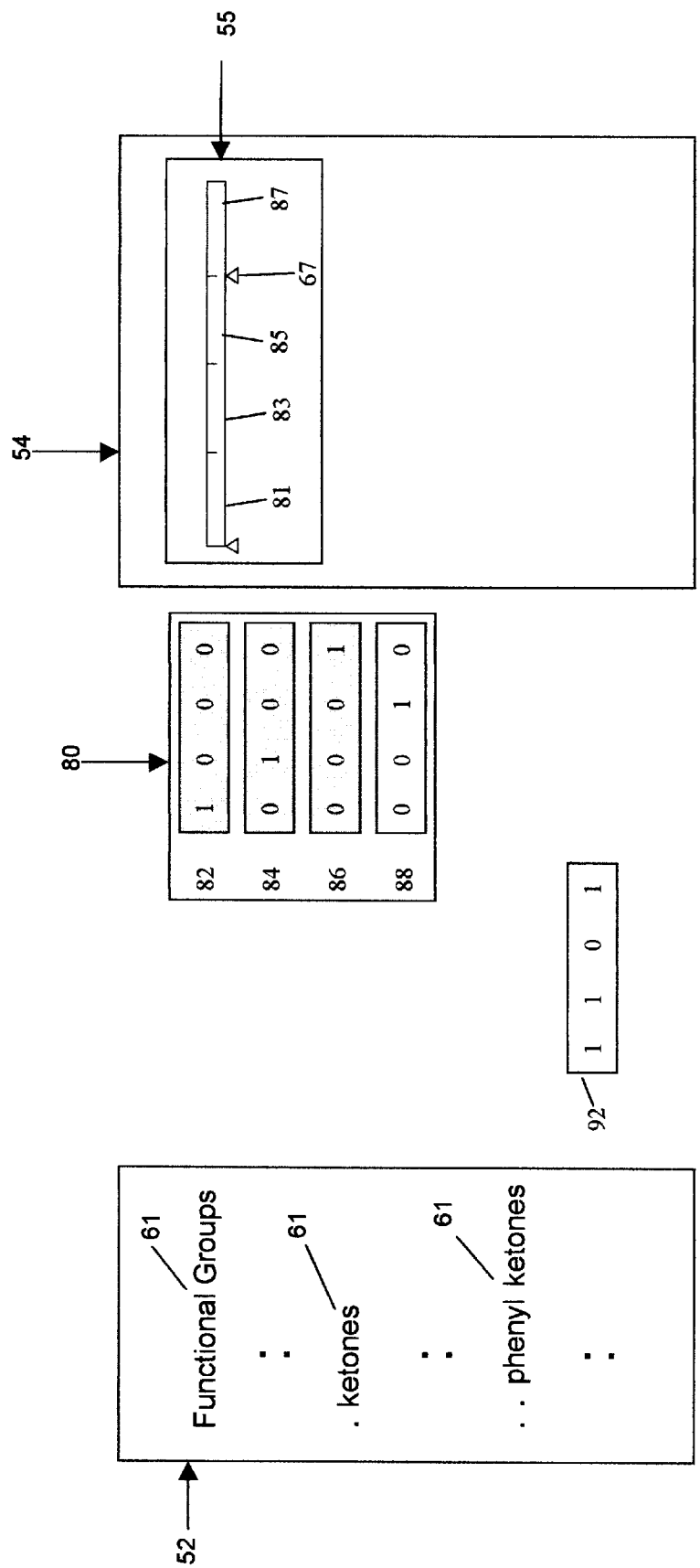
FIG. 3 shows bit vector representations of substance sets for features and properties.

FIG. 3 illustrates use of bit vectors for encoding the several property value ranges of a filter 55. The values for a property associated with a filter are divided into a fixed number of quanta (bins) 81, 83, 85, 87. For discrete values, such as the categories in activity data, each quanta represents a category. For continuous valued properties, such as molecular weight, the number of quanta and the boundaries are defined by the user. The property represented by filter 55 has four quanta 81, 83, 85, 87. The bit vector 82 represents the subset of substances with property values in the range of quanta 81. The kth bit is set to one if the kth substance in the underlying set falls in the property value range (or category), and zero otherwise. The first substance, represented by bit 1, has a property value that falls within range of quanta 81; the values for the other three substances, represented by bits 2–4 in vector 82, fall outside this range. Analogously, there is a bit vector 92 representing the subset of substances containing each structural feature 61 in the first panel 52. The shading on bit vectors 82, 84 and 86 show the effect of the user moving the slider 67 to eliminate the property range 87 (bit vector 88).

Figure 4:
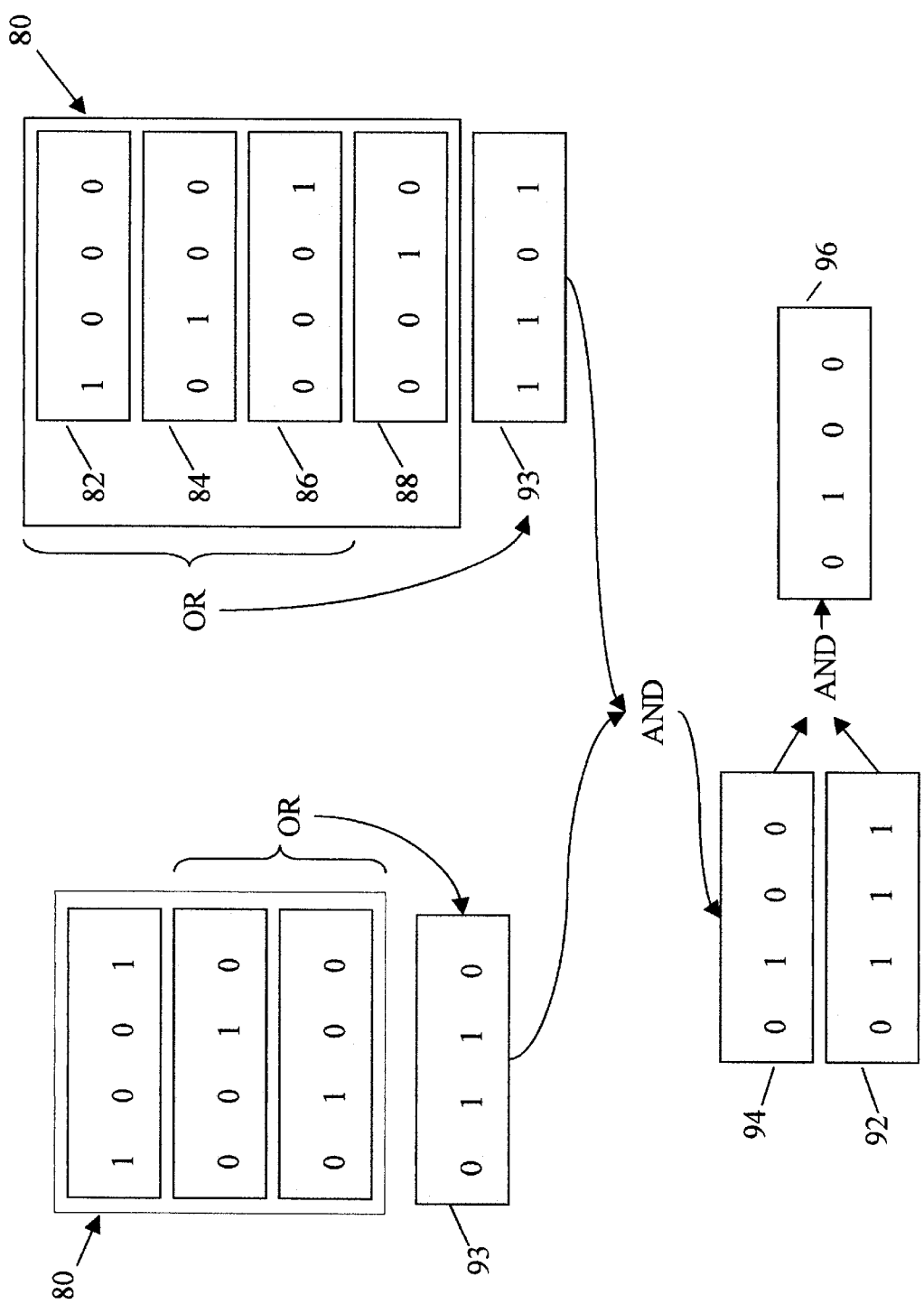
FIG. 4 is a diagram illustrating filter computation.

The use of bit vectors allows selection or combinations of subsets from the project and filtering calculations to be performed quickly. FIG. 4 illustrates the filter computation that is performed as part of the response to a user action such as opening a structural feature class in the first panel 52. The property filters represented by bit vector sets 80 are shaded to show the result of user movement of slider 67 (FIG. 3); for example, bit vector 88 has been eliminated (hence no shading). Bit vector 92 represents substance subset corresponding to a feature 61 in the feature hierarchy in the first panel 52 (FIG. 3).

The filter computation is illustrated in FIG. 4. The software performs a logical OR operation on the shaded bit vectors representing the quanta between the lower and upper bounds selected by the user with the slider 67 in the filter panel 55 (FIG. 3). The OR operation on bit vectors sets 80 yields resultant bit vectors 93. Next the system performs a logical AND operation on resultant bit vectors 93 yielding the filter subset bit vector 94 which is exactly the set of substances satisfying all property restrictions set by the user in the filters panel 55 (FIG. 2). Other logical operations could be used. For example, a logical OR operation would result in the set of substances satisfying at least one filter setting. Finally, the system performs a logical AND operation of the filter subset bit vector 94 and the structural feature subset bit vector 92 to produce the filtered output subset bit vector 96. This is the set of substances containing the structural feature and satisfying all property restrictions and is passed to the encoding step of the UI described above.

Figure 5:
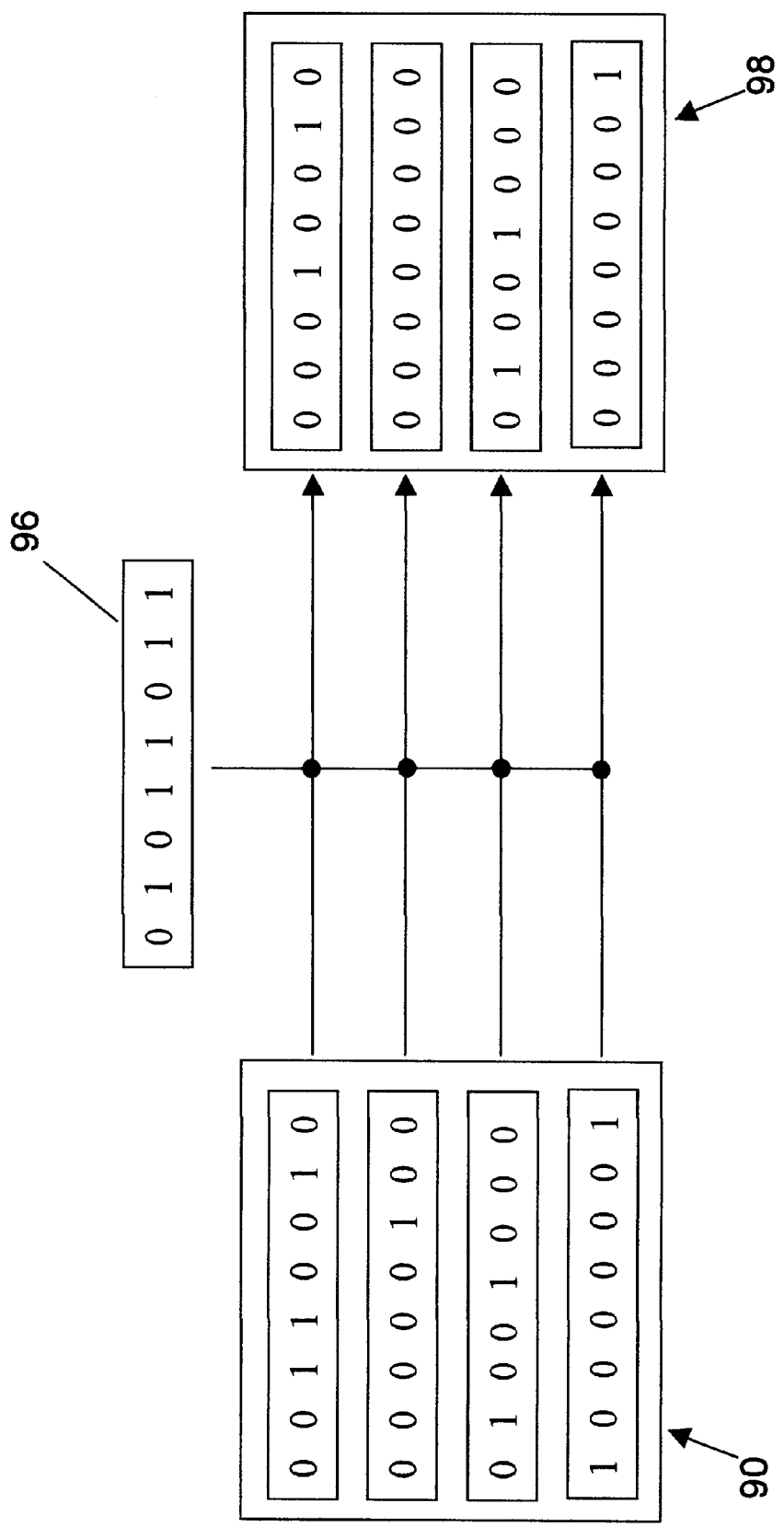
FIG. 5 is a diagram showing bit vector computations of features and activity categories.

FIG. 5 illustrates further bit vector operations that are performed in the encoding stage if the user has imported substance activity data into the project to correlate with features and/or properties. FIG. 5 shows a set of bit vectors 90 representing several activity categories. It also shows a bit vector 96 resulting from the filtering computation. The system performs a separate logical AND operation of the filter subset bit vector 96 and each of the activity category bit vectors 90 to produce a set of bit vectors 98 representing the set of filtered substances partitioned over the activity categories. The system counts one bits in each category and calculates the mean activity of the filter subset. These results are then used to calculate a p-value or the number of standard deviations by a standard statistical technique such as the Cochran-Mantel-Haenszel Row Mean Score test [10].

Figure 6:
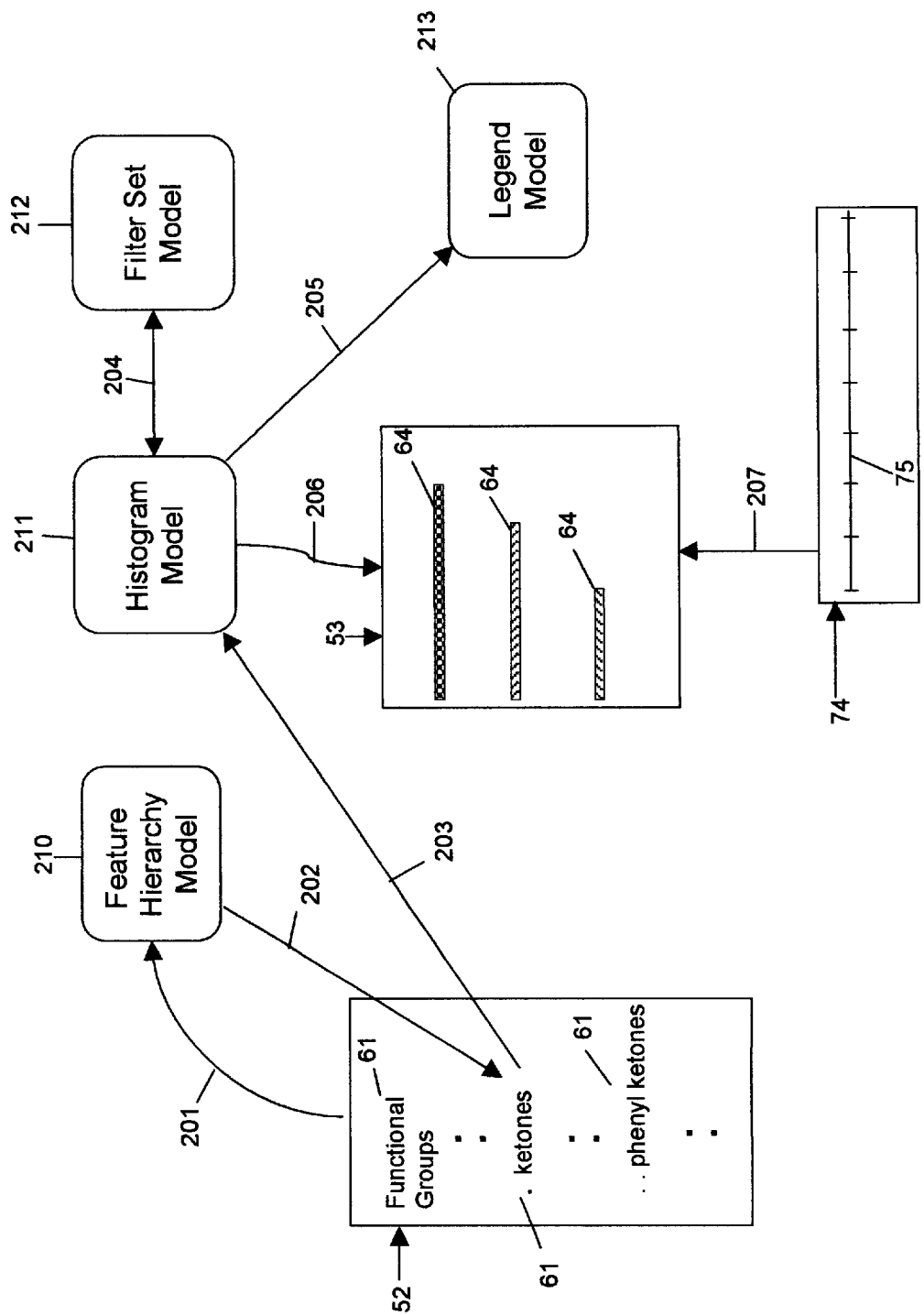
FIG. 6 is a diagram of an expanded node in the feature hierarchy.

FIG. 6 illustrates the actions performed by the software when browsing the feature hierarchy in histogram view as the user opens a class node in the feature hierarchy to expose members of the class. The user clicks on a node 61 in the feature hierarchy view (the first panel 52). The view sends a request 201 for the children of the node from feature hierarchy model 210 which replies 202 with a list of the children nodes. The feature hierarchy view 52 informs 203 the histogram model 211 that its state has changed and passes to it the changed rows and the feature identifiers. The histogram model 211 retrieves the structure subsets corresponding to these features from its cache or the server 10 (shown in FIG. 1). The histogram model 211 retrieves 204 the state of the filter set model 212 and performs the filter computation as described above. For each changed row, it computes a new filtered subset. For each row, it passes 205 the new filtered subset to the legend model 213 which determines the encoding category and graphical representation. The histogram model informs 206 the histogram view 53 that its state has changed. The histogram view 53 retrieves the summary data structure for each row. The histogram view 53 retrieves 207 from the number scale view 74 the coordinates of each number on its scale in order to determine where to position the end of the bar and renders the histogram bar 64.

Figure 7:
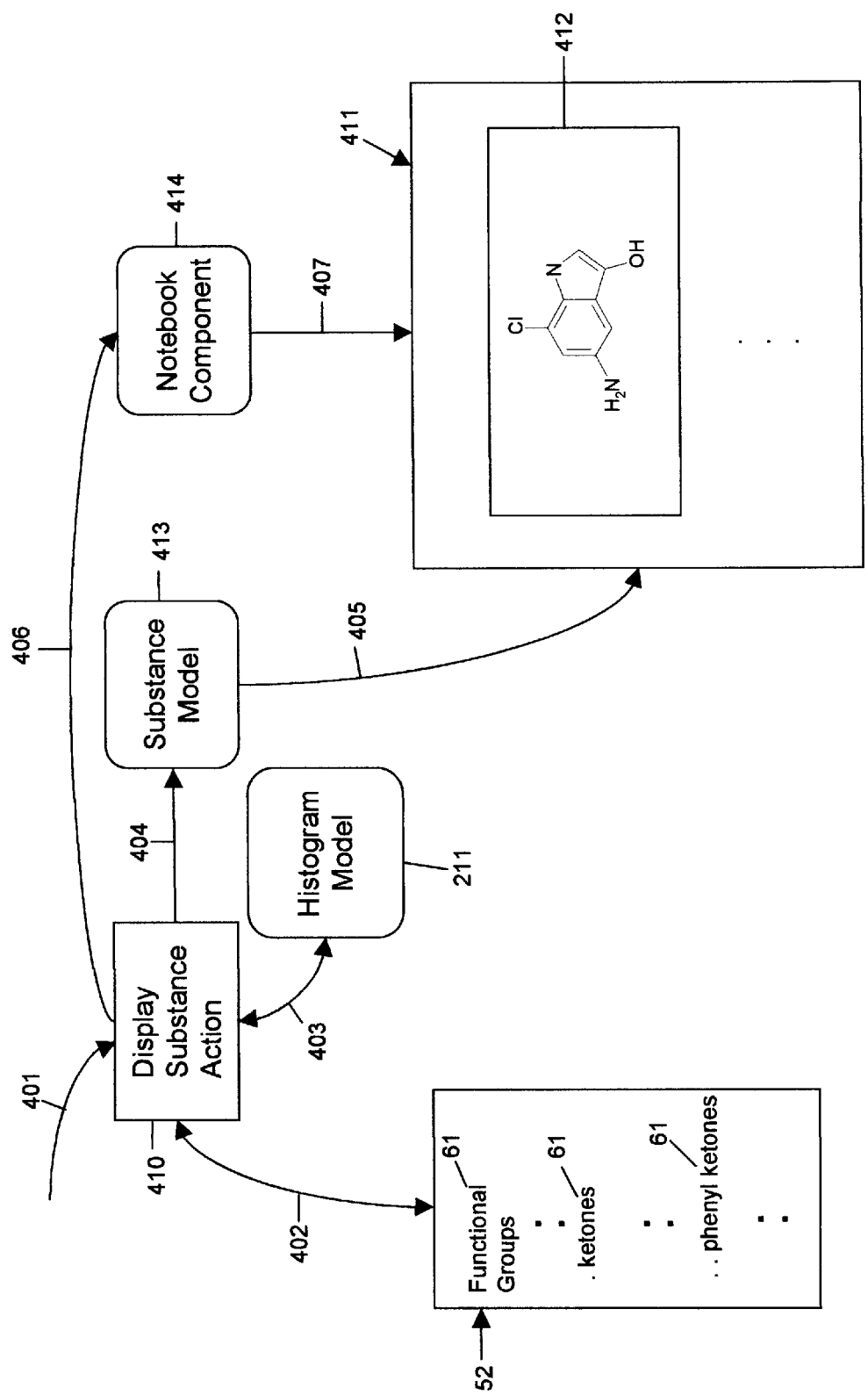
FIG. 7 is a diagram of the display substance details.

FIG. 7 illustrates the actions performed when the user selects the menu item which invokes the 'display as substances' action to display the detail of substances in the subset corresponding to the selected feature. The system invokes 401 the display-as-substances action 410 in response to the user's selection of the menu item. The action retrieves 402 the selected feature name 61 from the feature hierarchy view 52 and the structure subset associated with the feature from the histogram model 211. Both the name and the structure subset are passed 404 to the substance model 413, which retrieves the detailed data structure for each substance. The substance model 413 then notifies 405 the substance view 411 that its state has changed. The substance view 411 retrieves the data structures for as many substances that will fit in the display and passes these to the structure drawing functions (not shown). The structure drawing functions render these in the display space 412. The display-as-substances action 410 requests 406 the notebook component 414 to switch sheets. The notebook component 414 delegates this request to the component which manages the tabbed panes (not shown).

Figure 8:
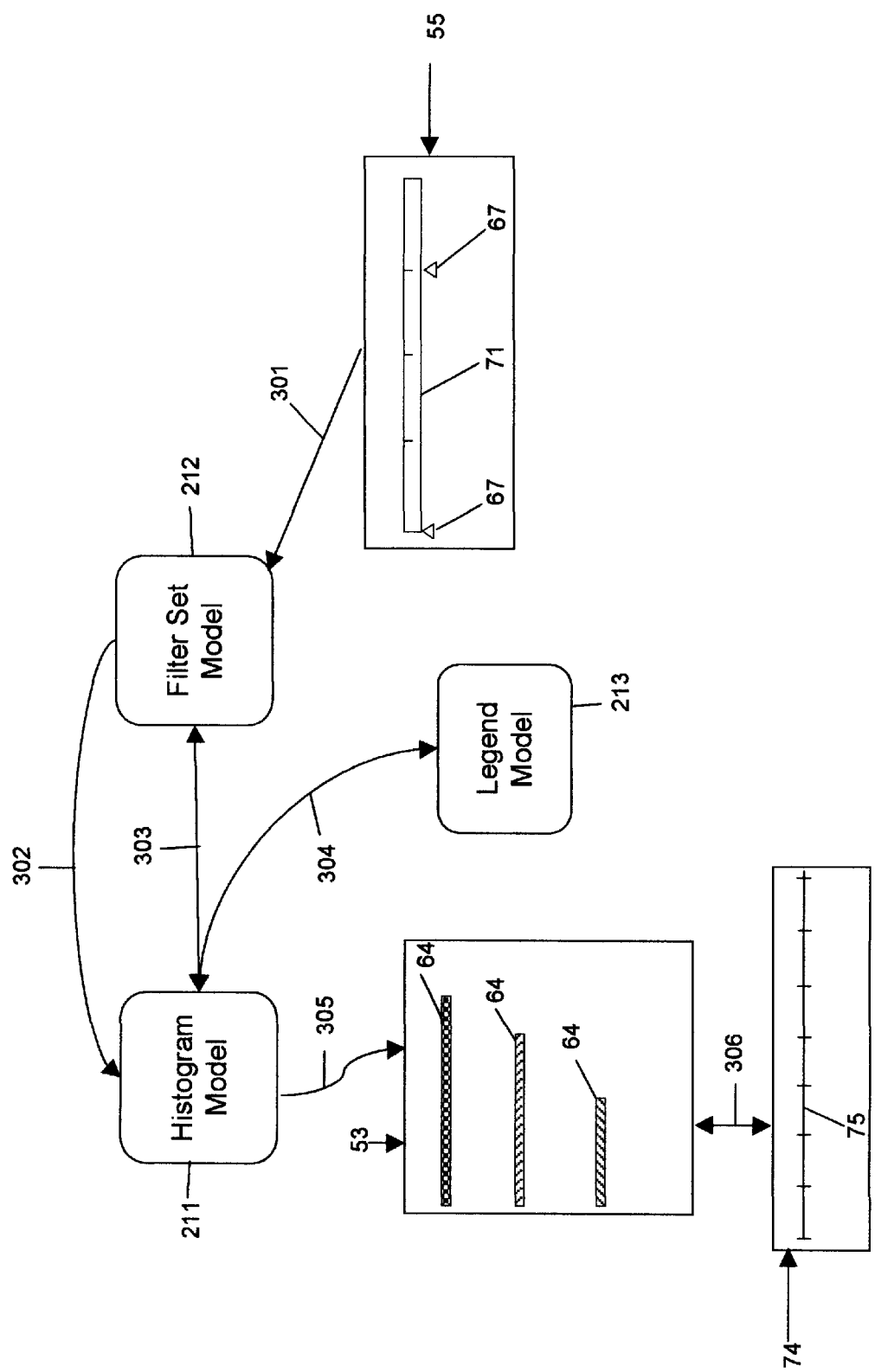
FIG. 8 is a diagram showing the use of a filter in the histogram view.

FIG. 8 illustrates the actions performed to constrain the members of subsets in a histogram view as the user moves a control 67 in a filter 55. The user moves the slider 67 on the slider into a new quanta. As the knob passes a tick mark, the filter view 55 informs 301 the filter set model 212 that its state has changed. The filter set model 212 notifies the histogram model 211 that a change has taken place and the filter in which the change occurred. The histogram model 211 performs the filtering, encoding 304, and rendering 306 as described above. The sequence is similar for scatterplots (not shown) except that each row is subdivided into a set of cells. The scatterplot view replaces the histogram view and has its own rendering functions, the scatterplot model replaces the histogram model and maintains a data structure for tables, and the x-axis is either a property or a feature hierarchy view.

There is further disclosed a method wherein the structural features displayed in the first panel 52 (FIG. 2) can be dynamically rearranged by the user. For example, the hierarchical organization can be removed (flattened); members of a branch can be sorted in a variety of ways, such as by average molecular weight; and the hierarchy or list can be filtered, removing features not satisfying a set of structural constraints, such as presence of a chlorine atom. The panel may also be equipped with standard devices for navigating the hierarchy or list such as a scroll bar and a "Find" window.

Figure 9:
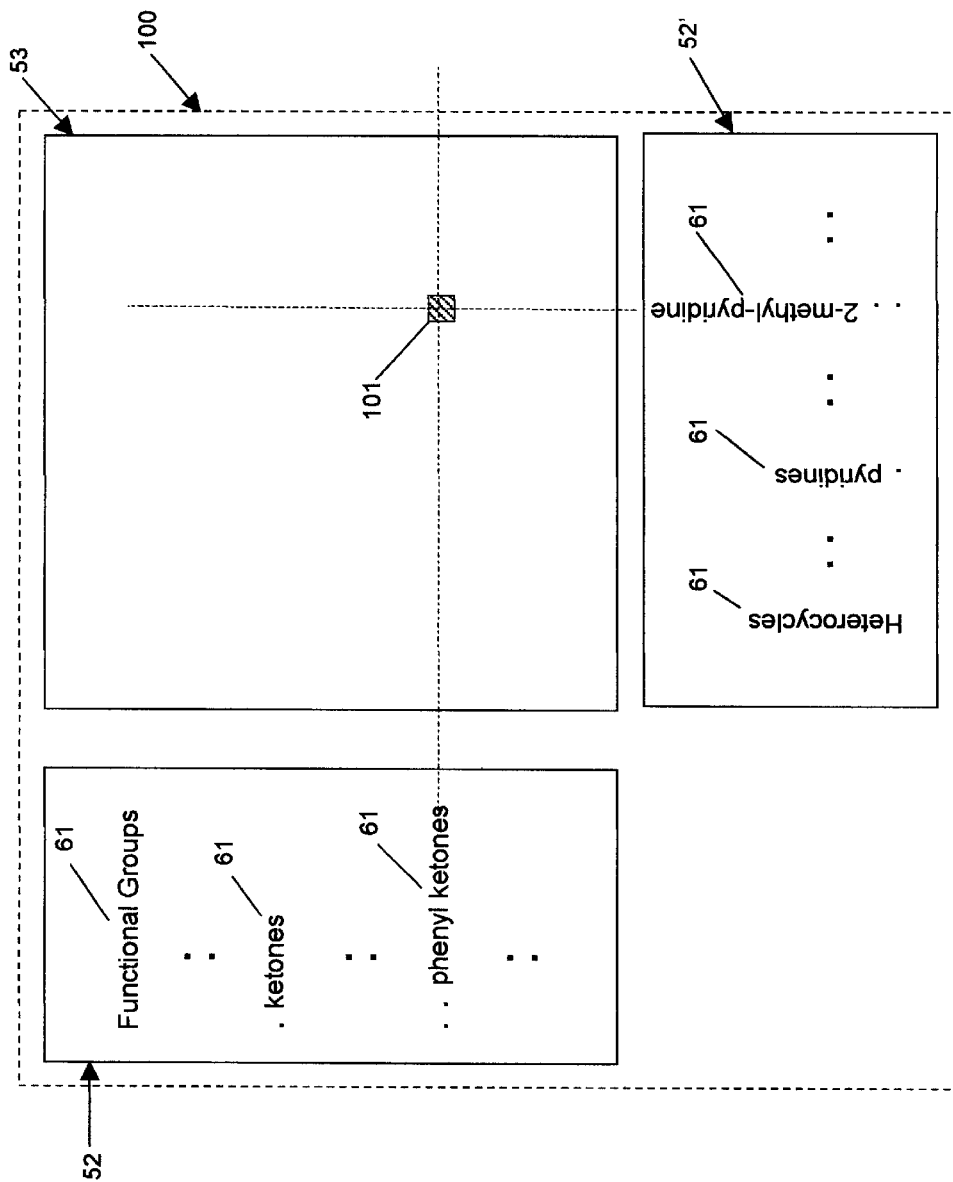
FIG. 9 is a schematic diagram of the scatterplot sheet.

There is yet further disclosed a method to visualize multi-dimensional information in the graphical display panel 53 as illustrated in FIG. 9. If there is a second panel of the first type 52', then there is a graphical element 101, such as a square, representing each pair of feature/properties, one from each of the panels of the first type 52 and 52'; and the square and both feature/properties are physically aligned and coordinated. The graphical element 101 shown as a square or box at the intersection of the two axes represents the sets of structures containing both feature/properties 61. For example, if the horizontal and the vertical axes both contain structural features, then the box would represent a collection of substances containing both features. If one axis contains structural features and the other axis contains property ranges, then the box represents the collection of substances which contain both the structural feature and are within the property range. Finally, if the axes both contain properties, then the box represents the collection of substances that are within the ranges of both properties. Any property used as a filter control may be used interchangeably as an axis for a scatterplot.

Figure 10:
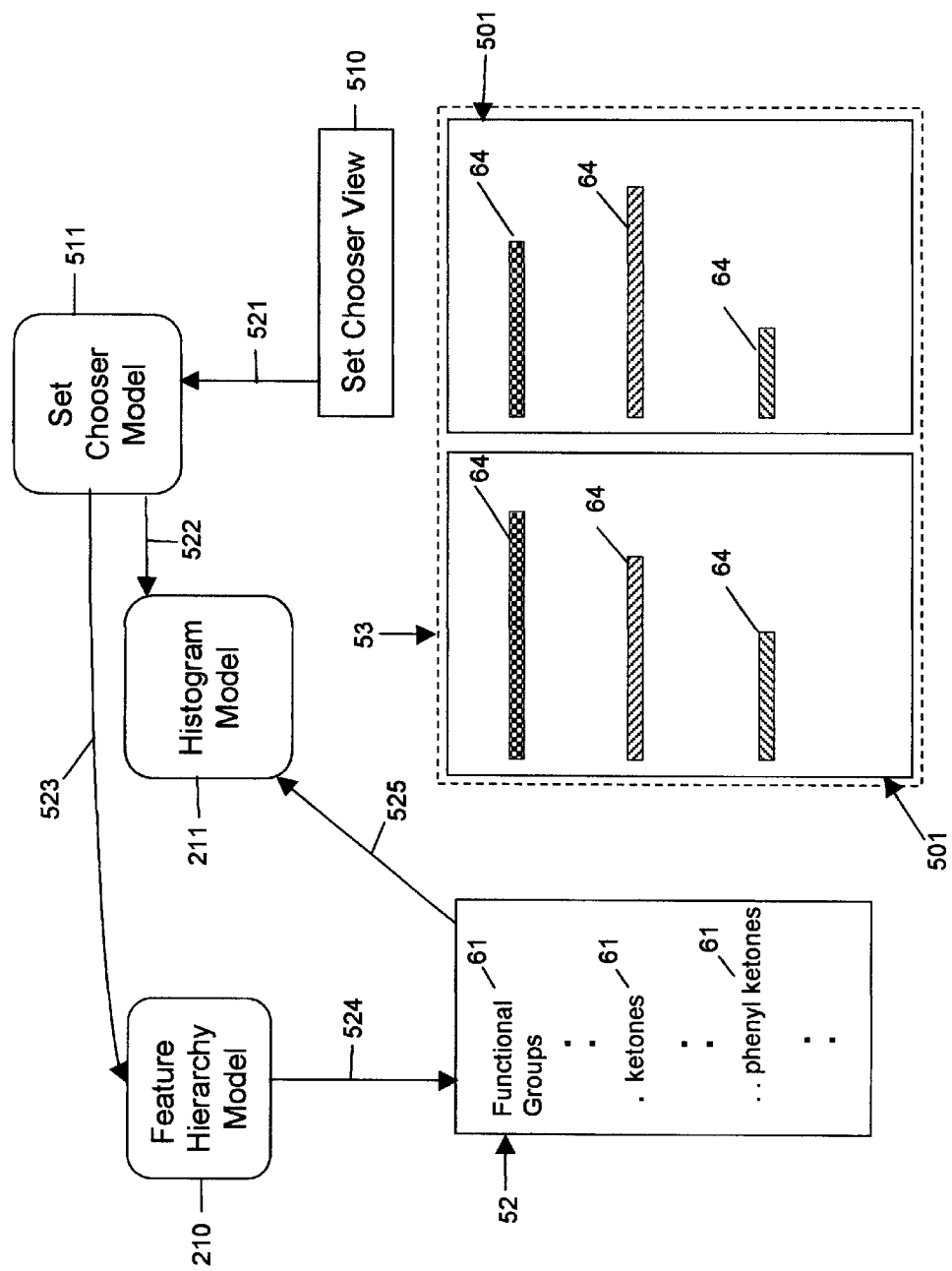
FIG. 10 is a diagram of the comparison of two sets in the histogram view.

The graphical display panel 53 in FIG. 10 may be divided vertically into two (or more) subpanels 501 to show two (or more) sets of structures allowing the user to compare the similarities and differences of the features in two structure sets side-by-side. FIG. 10 illustrates the actions performed when the user selects a second project in a set chooser (pull-down menu) in the histogram sheet. The set chooser view 510 notifies 521 set chooser model 511 that a new selection has been made. The set chooser model 511 notifies 522 and 523 components interested in the opening of a new set, namely the histogram model 211 and the feature hierarchy model 210, that a second set is being opened. Each model modifies its internal state to accommodate the additional set. The feature hierarchy model 210 requests that the server 10 (shown in FIG. 1) send it a new feature hierarchy formed by merging the hierarchies of the two projects and installs this merged hierarchy in view 52. The feature hierarchy model 210 notifies 524 its view 52 that the hierarchy has changed. Its view retrieves the top level nodes of the new hierarchy and displays them to the user. The feature hierarchy view 52 notifies 525 the histogram model 211 that its view has changed. The histogram model 211 retrieves the feature list from the view 52 and updates its internal models for both sets. The steps for filter-encode-render are then performed, except that the data structures for the new set are added to the data structures for the initial set. In an analogous way, the subpanels 501 may show parallel scatterplots, for example, plotting structural features on the vertical axis and molecular weight on the horizontal axis. In this case, each subpanel will be equipped with a separate horizontal molecular weight scale.

There is further disclosed several mechanisms for selecting and exploring subsets. For example, the user can select one or more features, then instruct the UI to create and open a new subproject (window) containing only those substances containing the selected features. Alternatively, the user can select one or more features, then instruct the UI to create and open a new subproject with all substances except those containing the selected feature(s). The user may specify any combination of structural features and filter property ranges as selection criteria for including substances in or excluding substances from a new subproject. In a further embodiment of the invention there are means for selecting a range of contiguous terms in a branch, several non-contiguous terms, or all terms in a branch. Within a subproject, the same capabilities are available as in the full project, but the statistical calculations reflect just the subpopulation.

Figure 11:
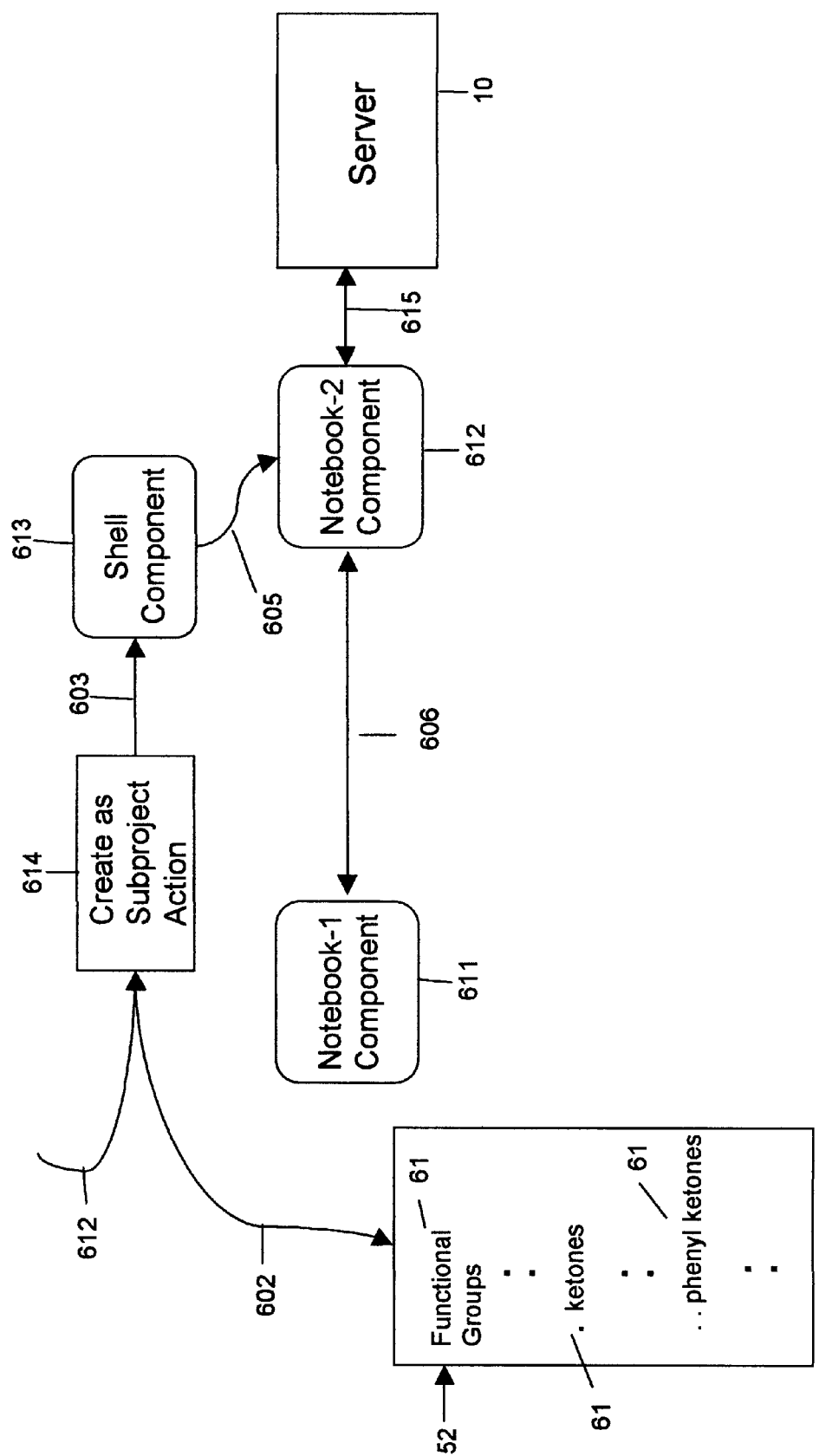
FIG. 11 is a diagram showing creation of a subproject.

FIG. 11 illustrates the actions performed when the user selects the menu item which invokes the 'create as subproject' action. The system invokes the create-as-subproject action 614 in response to the user's selection of the menu item. The create-as-subproject action 614 retrieves 602 the selected feature names 61 from the feature hierarchy view 52. For this example we will assume the user has selected phenyl ketones in a project called PROJ1. The create-as-subproject action 614 request 603 the shell component 613 to create a new subproject, passing it the feature phenyl ketones as the basis for the subproject. The shell component 613 creates a new notebook component 612. The shell component 613 requests 605 that notebook component 612 open a subproject based on the feature phenyl ketones. Notebook component 612 retrieves 606 the project name from the first notebook component 611 and its filter models. From the server 10, notebook component 612 retrieves 615 the structure subset containing phenyl ketones in the PROJ1 project. Using the filter models from the first notebook component 611, the second notebook component 612 computes a new set of structures using the filter computation described above. Finally, the second notebook component 612 invokes the 'open-subproject' function (not shown) to initialize its data models. This open-subproject function requests (not shown) of the server 10 a reduced feature hierarchy containing only the structures remaining after the filter computation.

The program according to the present invention allows the user to get detailed information on the dynamic state of the system. For example, if the medicinal chemist is unfamiliar with the meaning of a chemical name, the chemist can select the name and open a help window which shows the structural diagram and any restrictions on atoms, bonds or attached groups. Further, a feature can be selected and statistical information obtained such as the number of substances in each activity/property category, both filtered and unfiltered. In addition, a window can be accessed with details on individual substances in the current set containing that feature. Both features and the visual elements encoded by the legend, such as histogram bars or segments of bars, are selectable so that the subsets they represent can be examined in further detail.

In addition to displaying statistical correlations as standard deviation ranges, the system can also report p-values. The system could compare, for example, the average potency of the subset containing a specific structural feature to what would be expected if the subset was selected completely at random from the collection. The p-value is the probability that the subset, if selected by chance, would have average potency as high as or higher as that observed for the subset.

A key feature of the present invention is that the structural analysis performed during project creation 2 (shown in FIG. 1) is based on familiar structural features and combinations of features typically found in small molecule drug candidates. Table 3 sets forth a sample of the top level of the structural class hierarchy. In prior art programs, the molecular descriptors used for correlations, clustering and the like are often abstract. These theoretical constructs of the prior art are difficult for medicinal chemists to understand and visualize. A second key feature of the present invention is that the user has a convenient way to select and explore a succession of interesting subsets and to interactively control the contents of each subset using the filters. Because of these key features, the medicinal chemist can directly participate in the exploration process, using his or her intuition and experience to guide it. There is no provision for the chemist to participate in this process in the prior art programs. When the chemist is participating in the process, he or she will discover unexpected relationships that an algorithm, operating without the assistance of human intelligence and experience, would miss because the chemist will explore feature subsets that the algorithm would by-pass.

TABLE 3

Major Structural Classes

| | |
|---|---|
| Amino Acids | Heterocycles |
| Bases, nucleosides | Linker groups |
| Benzenes | Naphthalenes |
| Carbocycles | Natural products |
| Carbohydrates | Pharmacophores |
| Carbon chains | Toxic, reactive groups |
| Functional Groups | |

A novel feature of the invention is that it provides a visual framework which users may alter. Users may customize the properties associated with the interactive controls 55 (FIG. 2) and the axes 74 (FIG. 2).

Back-End Processes

The back-end processes are the three processes shown in FIG. 1: resource database compilation 1, project creation 2 and access to the compiled database 3 of chemical structures and related properties while a user is exploring a project.

Before any projects can be created in the preferred embodiment of the invention, the resources 4 used by the invention, such as templates for structural features, are pre-analyzed (compiled) and saved to an indexed file system. During project creation 2, the chemical structures from a chemical structures and properties database 7 designated by the user are analyzed to create a project. Each structure is broken down into features defined in the template library in the compiled chemical resources 6. All the associated data is computed, organized and saved to file for quick retrieval during project exploration. During project exploration 3, server manager 10 handles all requests from the client 11 for information to present to the user.

Glossary. As used herein and the claims the following terms shall have the recited meaning:
1. Feature means the atoms and bonds of a structure of the subject database 7 (shown in FIG. 1) that match a Template (as hereinafter defined).
2. Generic Atom means a defined set of atoms that map onto a single atom in the Pattern (as hereinafter defined).
3. Generic Group means a set of atoms, defined using Patterns, that map onto a single atom in the Pattern.
4. Leaf Node means an entry 61 (FIG. 2) in the hierarchy that does not have any children.
5. Non-Leaf Node means an entry 61 (FIG. 2) in the hierarchy that has children.
6. Pattern means a general substructure search definition.
7. Pattern Modifier means a substructure search restriction for a whole structure, sets of bonds and/or individual atoms and bonds.
8. Template is a Pattern for the structural Features recognized during project creation 2 (shown in FIG. 1) and available to the user as structural Feature terms 61 (FIG. 2).

Resource compilation item 1 in FIG. 1. The preferred embodiment of the invention has sets of structural definitions or patterns for: (1) aromatic systems (2) tautomeric systems (3) generic groups, and (4) Templates. Templates are the structural Features available to the user during project exploration. In the preferred embodiment of the invention, Patterns are defined using the MDL Molfile/SD format [11]. Atoms, within these Patterns, are either elements, generic groups that have been defined using other patterns or generic atoms like Ak (alkyl) and Ar (aryl). Additional restrictions, called Pattern Modifiers, are placed on the entire structure, sets of bonds and on individual atoms and bonds. Pattern Modifiers are defined in the data portion of the Molfile using techniques described in reference 7. Templates have their position in the Template hierarchy defined in the header portion of the Molfile as hereinafter described.

Before any project is created in the preferred embodiment of the invention, resources are converted to a form that can be efficiently used to create the invention's projects. A Template hierarchy for the entire set is computed using the Template's header information and saved to file. The compiled resources are saved to indexed binary files for quick access at the time of project creation.

With reference to FIG. 1, project creation 2 comprises the following steps:
1. Creation of the structure databases. For each structure in the project 7 the Templates are matched against the structure, using the standard substructure search techniques [5]. The shortest path between each pair of Features is computed. This information is then committed to the indexed file system.
2. Creation of the project feature hierarchy. A Feature hierarchy is created containing only Features that are either present in the set of structures or that are Non-Leaf Nodes where a child leaf is present.
3. Creation of the inverted structure/feature database. There is one entry in the project database 9 for each Feature. It contains the name and identifier of the Feature, along with the set of structures containing it. In addition, the structures are added to parent Feature entry (defined in the Feature hierarchy).
4. Creation of the databases for comparison. In order to efficiently compare two or more projects to determine the common substances, each substance is assigned a canonical number using techniques described in [7].
5. Importing properties. In the preferred embodiment of the invention, at least the following properties are calculated:
   (a) Molecular weight—the sum of atomic weights for all atoms including non-specified hydrogens.
   (b) Rotatable bonds—the number of single, non-terminal acyclic bonds
   (c) Number of hydrogen bond donors—defined by a generic group pattern; and
   (d) Number of hydrogen bond acceptors—defined by a generic group pattern. This results in a table where each row contains the substance identifier and the property value. In addition, user defined properties can be imported into the system.

In the preferred embodiment of the invention, the server manager 10 (shown in FIG. 1) is responsible for all requests for data from the client. The server manager 10 handles all requests for information about the projects that have been created. In addition, the server manager 10 handles the creation of the projects and subprojects and returns information to the client on the Templates, the structures and the hierarchies. Server manager 10 also handles all intensive back-end calculations like merging hierarchy and comparing structures in two or more different projects for common substances.

In the preferred embodiment of the invention, all structural information is stored and accessed by the server manager 10 using the structure class hierarchy that was constructed during project creation 2. The invention has no means for the user to enter a structural query into the system.

Template Library

The structural analysis performed during project creation 2 (shown in FIG. 1) is based on predefined molecular substructures (Templates) stored in a Template library. The full set of Templates is organized as a hierarchy. The top-level hierarchy lists the major structural classes. Each of these classes is comprised of subclasses which in turn may be comprised of further subclasses or individual substructural Features (Templates).

Each Leaf Node in the hierarchy has a structure and a chemical name. The structure is used by the project creation process 2 (shown in FIG. 1) to identify instances of the Feature in a database of chemical structures 7 (shown in FIG. 1) and to display a diagram of the Feature to the user. A Non-Leaf Node in the hierarchy may or may not have a structure. A node representing a specific structural class with a generic substituent such as 2-R-thiazole has a structure while general classes such as Heterocycles do not.

Template structures are represented and stored in a format based on MDL's Molfile/SD file format [11]. The first line of a Molfile is the Template name. The second line is a pair of integers which give the Template identifier and the identifier of the parent Template in the hierarchy.

Figure 12:
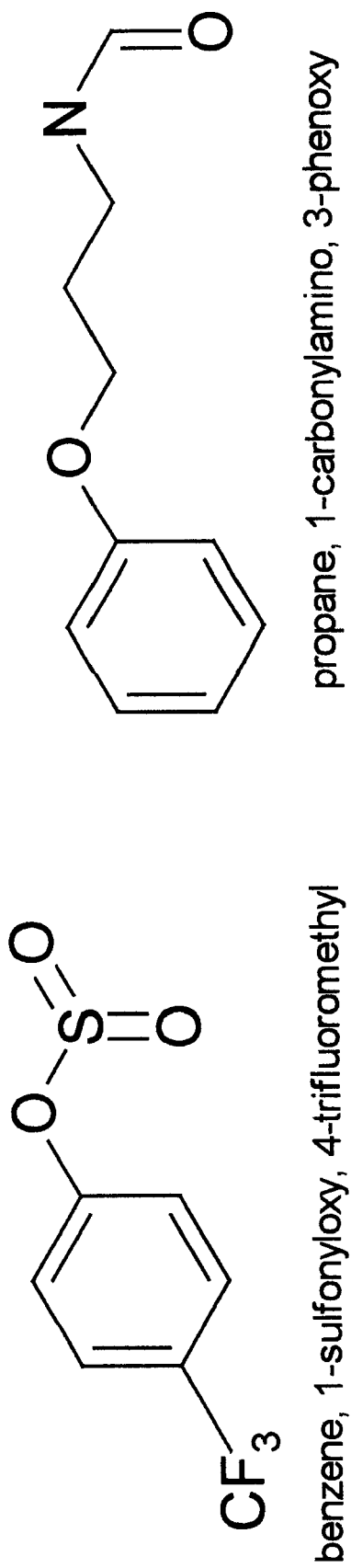
FIG. 12 shows examples of Template structure and chemical name.

Each Template has a chemical name generally based on the systematic nomenclature developed by Chemical Abstracts [6]. Most Templates are named as a parent plus substituent prefixes (radicals) written inverted for sorting. Compound radicals are named as base radical plus substituents [ref 6, ¶133] starting from the distal end (farthest from the point of attachment to the parent), as illustrated in the examples shown in FIG. 12.

EXAMPLE I

This example is provided to demonstrate the program and system of the invention. When the chemist first opens the UI with a project, the opening view is the top level of the structural class hierarchy in a panel. There may be about 25 categories visible at this level, however, tens of thousands of terms may be available in the full hierarchy. Histogram bars for each structural class give the number of substances in the dataset containing one or more instances of the Feature, plotted on a normal Cartesian scale or a log scale.

At this time, the user may wish to activate several property filters which the system presents as a series of two-ended sliders, arranged in a panel. The user may also select a property for color coding histogram bars (e.g., biological activity) and/or set statistical standard deviation ranges and the color of each range.

With these visual controls in place, the user begins to explore the structure hierarchy. There are several techniques the user may employ. The simplest is to just open a branch and visually scan for high frequency structural Features for which mean activity is higher than expected, especially in the highest standard deviation category.

The user can speed up the search for high activity Features by removing low frequency Features and branches that have been well-tested, flattening the hierarchy to a list, and sorting the Feature list on the number of standard deviations. Having identified several promising Features with acceptable frequencies and activity, the user may reset the original hierarchy for browsing and comparing the newly found Features with related, near-by Features in the hierarchy.

Alternatively, the user might decide to look for outliers, active substances in structural classes with low mean activity, Features with high activity that occur infrequently in this dataset, Features that are unusual in typical drug molecules or new compound classes with promising activity.

While browsing the user manipulates the slider controls to observe the effect on frequency and activity shown by color and length changes in the histogram bars. For example, the user may wish to focus on small, rigid molecules with low hydrogen bond acceptor/donor counts. The user can easily adjust the sliders to do this, first making gross adjustments to set the approximate range, then making fine adjustments using visual feedback from changes in the size and color of the histogram bars.

Having found a promising or otherwise interesting Feature class, say Feature X, the user will examine the class in greater detail. He or she can do so by creating a subproject with all the X-containing substances in the dataset, replicate the environment (property filters, legend, etc.) and begin exploring the subproject. This way he or she can find co-occurring Features that apparently further enhance activity or Features that apparently mask activity (those with unexpected low activity). However, the statistics in this subproject reflect only this subpopulation. Thus, any highly active (or highly inactive) Features found are judged relative to an already highly active subpopulation.

Alternatively, the user can load the X-Feature containing subset as two parallel subsets, with all actives in one panel and all inactives in the parallel panel. This technique allows the user to see more information on relative frequencies of actives versus inactives while browsing.

At this point, the user will have formulated a structural hypothesis that he or she believes can explain compound activity. He or she then designs a focused compound library using the structural hypothesis as a scaffold and comparing the virtual library with all compounds containing the hypothesis substructure that have already been tested. Once the design is complete, the user will also compare the virtual library with compounds in a corporate database that have not been tested and any commercially available compound sets.

As described above, the present invention Features a method whereby a user can load two (or more) sets of structures and compare them side-by-side in parallel sub-panels. This side-by-side comparison provides a convenient, visual method for finding holes in the new library that can be filled from the corporate database or a commercial library.

INDUSTRIAL APPLICABILITY

The present inventors, through extensive research, have developed a user interface which allows a user to browse the contents of a dataset on a computer, reduce the set down to an interesting subsets based on structural and property considerations, statistically correlate the structural Features with one or more biological or physical properties and compare the similarity and differences between two or more datasets. The present invention enhances a chemist's ability to analyze, organize and visualize large sets of chemical compounds and associated biological and/or physical property data. It is the application of this technology to the discovery of pharmaceuticals that represents a substantial advancement in the state of the art.

Having thus described the present invention in detail, it will be obvious to those skilled in the art that various changes or modifications may be made without departing from the scope of the invention defined in the appended claims and described in the specification.

We claim:

1. A computer system, for visualizing and exploring the structural analysis of chemical compounds and related properties of chemical compounds, comprising:
   (a) a compiled project comprising a database of chemical compounds that have been analyzed for the presence of predefined structural Features and related molecular properties;
   (b) a client computer program that functions as a user interface (UI), said client computer program adapted to display data from said compiled project regarding a set of substances that contain at least one Feature within a property value range; and
   (c) a server computer program that functions as a server for said compiledproject and computational engine.

2. The computer system according to claim 1 wherein said UI comprises at least three coordinating panels.

3. The computer system according to claim 2 wherein said UI comprises:
   (a) at least one first panel comprising said predefined structural Features or ranges of substance properties;
   (b) a second panel comprising a representation of the contents of the underlying substance set relative to said predefined structural Features or said properties in said first panel; and
   (c) a third panel comprising at least one interactive control that provides for the dynamic adjustment of members of said underlying substance set.

4. The computer system according to claim 1 wherein said compiled project comprises:
   a file of said predefined structural Features and a precompiled Feature hierarchy.

5. The computer system of claim 3 wherein said UI additionally contains a fourth panel for selecting and adjusting the meaning and appearance of the representation displayed in said second panel.

6. A method for selecting and exploring subsets of a project, said method comprising the steps of:
   (a) activating a client computer program which functions as a UI, said UI comprising a set of interactive controls,
   (b) loading a compiled project of substances analyzed in accordance with predefined structural Features and associated molecular properties into said computer program, said project compiled in accordance with said predefined structural Features defined using Templates,
   (c) and manipulating the interactive controls of said UI to select at least one subclass of substances from the underlying substance set in accordance with a Feature within a range of values for said associated properties and display data regarding the set of substances in the subclass of substances.

7. The method according to claim 6 wherein the said subclass is selected by manipulating the interactive controls of said UI to expose subclasses of said predefined structural Features and to restrict the property values of the substances in the underlying substance set.

8. The method according to claim 6 wherein the interactive controls of said UI are manipulated to create a new project from said subclass.

9. The method according to claim 6 wherein the interactive controls of said UI are manipulated to expose greater detail of the substances in said subclass.

10. A method for statistically correlating sets of chemical compounds containing certain structural Features defined using Templates with one or more molecular properties of the substances, said method comprising the steps of:
    (a) activating a client computer program which functions as a UI;
    (b) loading a compiled project of substances analyzed in accordance with predefined structural Features and associated molecular properties into said computer program;
    (c) selecting at least one substance property for correlation;
    (d) selecting a statistical measure; and
    (e) displaying a measure of correlation of the value for said selected substance property related to each structural Feature from said compiled project in accordance with said statistical measure.

11. A method for visually comparing the similarity and differences of two or more projects defined in accordance with structural Features and Templates, said method comprising the steps of:
    (a) activating a client computer program which functions as a UI;
    (b) loading a compiled project of substances analyzed in accordance with predefined structural Features and associated molecular properties into said computer program;
    (c) loading at least one additional compiled project of substances analyzed in accordance with the same predefined structural Features and associated molecular properties;
    (d) selecting a property range for each compiled project; and
    (e) graphically displaying data regarding the set of substances in each of said projects in accordance with said predefined structural Features and said selected property ranges.

* * * * *

UNITED STATES PATENT AND TRADEMARK OFFICE
CERTIFICATE OF CORRECTION

PATENT NO. : 6,323,852 B1
DATED : November 27, 2001
INVENTOR(S) : Blower, Jr. et al.

It is certified that error appears in the above-identified patent and that said Letters Patent is hereby corrected as shown below:

<u>Column 18,</u>
Please insert the following annex of information at the end of the patent:
REFERENCES 1. Ahlberg, C., & Shneiderman, B. (1994). "Visual information seeking: Tight coupling of dynamic query filters with starfield displays." Proceedings of the CHI'94 Conference on Human Factors in Computing Systems, 313-317. New York: ACM.
2. Ahlberg, C., & Wistrand, E. (1995). "IVEE: An environment for automatic creations of dynamic queries applications," Proceedings of the CHI'94 Conference on Human Factors in Computing Systems, 15-16. New York: ACM.
3. Shneiderman, Ben. (1998). Designing the User Interface: Strategies for Effective Human-Computer Interaction. 3rd edition. Addison-Wesley.
4. Chuah, M. C., Kerpedjiev, S., Kolojejchick, J., Lucas, P., Roth, S. F. (1997) "Toward an Information Visualization Workspace: combining Multiple Means of Expression", Human-Computer Interaction, 12(1 & 2), pp. 131-186.
5. Stobaugh, R.E. "Chemical Structure Searching," J. Chem. Inf. Comput. Sci., 1985, 25, 271-275
6. Chemical Abstracts Index Guide, Appendix IV, Chemical Substance Index Names, American Chemical Society, 1997.
7. Myatt, G.J., "Computer Aided Estimation of Synthetic Accessibility," Ph.D. Thesis, Leeds University, 1994
8. Kubinyi, H. QSAR: Hansch Analysis and Related Approaches, VCH Publishers, New York, 1993.
9. Hawkins, D. M.; Young, S. S.; Rusinko III, A. "Analysis of a Large Structure-Activity Data Set Using Recursive Partitioning," Quant. Struct.-Act. Relat. 1997, 16, 1-7.
10. Agresti, A. Categorical Data Analysis, John Wiley & Sons Inc., New York, 1990, pp. 286-287.
11. Dalby, A., Nourse, J.G., Hounshell, W.D., Gushurst, A.K.I., Grier, D.L., Leland, B.A. and Laufer, J. J. Chem. Inf. Comput. Sci., 1992, 32, 244-255.

Signed and Sealed this

Fifteenth Day of July, 2003

JAMES E. ROGAN
*Director of the United States Patent and Trademark Office*